United States Patent
Atlan et al.

(10) Patent No.: US 9,733,064 B2
(45) Date of Patent: Aug. 15, 2017

(54) DIGITAL OFF-AXIS HETERODYNE HOLOGRAPHIC INTERFEROMETRY FOR DETECTING VIBRATION AMPLITUDE

(71) Applicant: Centre National de la Recherche Scientifique—CNRS, Paris (FR)

(72) Inventors: Michael Atlan, Paris (FR); Benjamin Samson, Paris (FR)

(73) Assignee: CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 70 days.

(21) Appl. No.: 14/442,910

(22) PCT Filed: Nov. 15, 2013

(86) PCT No.: PCT/EP2013/073978
§ 371 (c)(1),
(2) Date: May 14, 2015

(87) PCT Pub. No.: WO2014/076251
PCT Pub. Date: May 22, 2014

(65) Prior Publication Data
US 2015/0292858 A1    Oct. 15, 2015

(30) Foreign Application Priority Data
Nov. 15, 2012  (FR) ..................... 12 60883

(51) Int. Cl.
*G01B 9/02* (2006.01)
*G01B 9/021* (2006.01)
(Continued)

(52) U.S. Cl.
CPC .......... *G01B 9/021* (2013.01); *G01N 21/453* (2013.01); *G03H 1/0005* (2013.01);
(Continued)

(58) Field of Classification Search
CPC .... G01B 9/021; G01N 21/453; G03H 1/0005; G03H 1/0866; G03H 1/0443;
(Continued)

(56) References Cited

PUBLICATIONS

International Search Report in corresponding PCT Application No. PCT/EP2013/073978 mailed Feb. 5, 2014 (2 pages).
(Continued)

*Primary Examiner* — Hwa Lee
(74) *Attorney, Agent, or Firm* — Osha Liang LLP

(57) ABSTRACT

The invention relates to a digital holography method for detecting the vibration amplitude of an object (15) having a vibration frequency ω, comprising: generating object illumination waves ($W_I$) and reference waves ($W_{LO}$); acquiring interferograms between the reference wave ($W_{LO}$) and a signal wave ($W_s$) by means of a bandwidth ω s detector (19), the reference wave comprising two components $E_{LO1}$, $E_{LO1}$ of frequencies $\omega_1$, $\omega_2$ that are respectively staggered in relation to the laser frequency $\omega_L$ by a quantity $\delta_1 = \gamma_1 \omega_s$ and $\delta_2 = q\omega + \gamma 2\omega_s$, where q is an integer and $-0.5 \leq \gamma 1, \gamma_2 \leq 0.5$; and calculating the vibration amplitude of the object from the optical beats spectrum deduced from the complex amplitude of an interferogram.

16 Claims, 7 Drawing Sheets

(51) Int. Cl.
  *G03H 1/00* (2006.01)
  *G03H 1/08* (2006.01)
  *G01N 21/45* (2006.01)
  *G03H 1/04* (2006.01)

(52) U.S. Cl.
  CPC ......... *G03H 1/0443* (2013.01); *G03H 1/0866* (2013.01); *G03H 2001/0033* (2013.01); *G03H 2001/0456* (2013.01); *G03H 2001/0463* (2013.01); *G03H 2210/62* (2013.01); *G03H 2227/03* (2013.01)

(58) Field of Classification Search
  CPC ....... G03H 2210/62; G03H 2001/0033; G03H 2227/03; G03H 2001/0463; G03H 2001/0456
  See application file for complete search history.

(56) References Cited

PUBLICATIONS

Pavel Psota et al.; "Measurement of Piezoelectric Transformer Vibrations by Digital Holography"; IEEE Transactions on Ultrasonics, Ferroelectrics and Frequency Control, vol. 59, No. 9; Sep. 2012; pp. 1962-1968 (7 pages).

Benjamin Samson et al.; "Video-rate laser Doppler vibrometry by heterodyne holography"; Optics Letters, The Optical Society, vol. 36, No. 8; Apr. 15, 2011; pp. 1449-1451 (3 pages).

Vit Ledl et al.; "Frequency Shifted Digital Holography for the Measurement of Vibration with Very Small Amplitudes"; AIP Conference Proceedings; Jan. 1, 2010; pp. 415-419 (5 pages).

M. Atlan et al.; "High-speed wave-mixing laser Doppler imaging in vivo"; Optics Letters; vol. 33, No. 8; Apr. 15, 2008; pp. 842-844 (3 pages).

Written Opinion in corresponding PCT Application No. PCT/EP2013/073978 mailed Feb. 5, 2014 (8 pages).

DIGITAL OFF-AXIS HETERODYNE HOLOGRAPHIC INTERFEROMETRY FOR DETECTING VIBRATION AMPLITUDE

TECHNICAL FIELD OF THE INVENTION

The present invention relates to a digital off-axis heterodyne holographic interferometry device and method, in particular for measuring mechanical vibrations of nanometric amplitudes.

PRIOR ART

Holography is a method which makes it possible to reconstruct an image in three dimensions (3D) of an object from the recording of an interference figure between two coherent waves, a reference wave and a wave diffused by the object to be observed. In the case of conventional holographic interferometry, the recording is performed on a photographic plate. Once the plate is developed by known photography methods, a hologram is obtained. The 3D image is reconstructed by illuminating the hologram with the reference wave which then produces a wave directly transmitted (order 0) and two diffracted light waves, an object wave (or signal wave) which reconstitutes a virtual image of the object and a conjugate wave which forms a parasitic real image which hampers the observation of the virtual image and whose elimination is sought. In conventional holography, the use for example of a thick material for the photographic emulsion used to record the hologram makes it possible to create a volume hologram which, upon restitution, will diffract only the signal wave sought. Images of very high quality are thus obtained. However, in conventional holography, the quantitative information recorded (amplitude and phase of the signal wave) is not directly accessible, which limits the applications thereof.

In order to have useable quantitative information, a novel holography technique has emerged, called digital holography, in which the photographic film is replaced by a two-dimensional optoelectronic detector, for example a CCD camera. The acquisition of the interference signal by the detector makes it possible to form an interferogram, that is to say a sampled interference figure on the two-dimensional detector. The entirely digital reconstruction method consists in calculating, from the interferogram, the field of the diffracted wave in a plane of the object, for example by means of a Fresnel transform, which can, for example, comprise a fast Fourier transform (FFT) algorithm. An example of digital holography is disclosed in Schnars and Jüptner, "Direct recording of holograms by a COD target and numerical reconstruction", Appl. Opt. 33, p. 179-181 (1994). Digital holography offers numerous advantages compared to conventional holography, notably because the reconstructed field of the signal wave is a complex function making it possible to access the amplitude and the phase of the signal wave. It is thus possible to establish the three-dimensional mapping of an object, to study objects in motion and notably a vibrating object. However, in the same way as in thin film conventional holography, the field of the signal wave calculated from the interferogram simultaneously comprises the diffractive order sought, the order 0, and the parasitic conjugate order. There is therefore an uncertainty as to the complex amplitude of the object wave that is to be determined.

One way of eliminating the parasitic conjugate image and the non-diffractive wave is to introduce a phase shift between the reference wave and the signal wave. In the application EP 1 043 632 for example, a so-called digital heterodyne holography technique is described, notably for application to the study of vibrating objects. According to this technique, the frequency of the reference wave is offset by a quantity determined as a function of the vibration frequency of the object and of the rate of acquisition of the detector, for example by means of two acousto-optical modulators. A digital demodulation of the interferogram then makes it possible to eliminate the components due to the order 0 and the conjugate order.

To gain even more accuracy, it has been proposed (see for example M. Gross et al., "Digital Holography with ultimate sensibility", Optics Letters, vol. 32 (2007)), to combine the digital heterodyne holography technique with an off-axis holography technique, in which an angle (typically a few degrees) is introduced between the reference wave and the wave diffused by the object. Coupled with a digital spatial filtering, this technique makes it possible to filter the zero order transmitted wave as well as the noise which is attached to it. It is then possible to record and reconstruct holographic images with a better signal-to-noise ratio, making it possible to measure vibrations of very low amplitude, at video acquisition rate. In the article by V. Lédl et al. ("Frequency Shifted Digital Holography for the Measurement of Vibration with Very Small Amplitudes", $9^{th}$ International Conference on Vibration Measurements by Laser and Noncontact Techniques, June 2010), measurements of vibration amplitudes of the order of a nanometer have thus been performed experimentally, by using an off-axis heterodyne holography set-up.

The invention proposes an off-axis heterodyne holography method and device that make it possible, compared to the known techniques, to access higher signal-to-noise ratios and to thereby gain in measurement accuracy, notably on vibration amplitudes of less than a nanometer.

SUMMARY OF THE INVENTION

According to a first aspect, the invention relates to a digital holography method for detecting the amplitude z of vibration of an object at least one vibration frequency ω, comprising:

the generation of an object illumination laser wave of frequency $\omega_L$ and of a reference wave coherent with the illumination wave (that is to say, exhibiting a non-random phase relationship with the illumination wave);

the acquisition, by means of a two-dimensional optoelectronic detector of temporal bandwidth $\omega_s$, of a set of interferograms resulting from the interference of the reference wave and of a signal wave from the object, the signal and reference waves exhibiting an angular shift, the field of the reference wave comprising a first component of frequency $\omega_1$ and at least one second component of frequency $\omega_2$, the frequencies $\omega_1$ and $\omega_2$ being offset from the frequency $\omega_L$ of the laser wave respectively by a determined quantity $\delta_1$, $\delta_2$, with $\delta_1 = \gamma_1 \omega_s$ and $\delta_2 = q\omega + \gamma_2 \omega_s$, where q is a relative integer and $-0.5 \leq \gamma_1, \gamma_2 \leq 0.5$; and the processing of the interferograms comprising:

the calculation of a hologram of the object from each interferogram, the hologram being defined by the complex amplitude of the signal wave in a given spatial field of a plane of the object;

the calculation of the time-frequency Fourier transform of the complex amplitudes of said holograms, making it possible to obtain, at each point of the spatial field, a frequency spectrum of the optical beats between the frequency components of the reference wave and of the signal wave, the optical beats spectrum comprising at least two bands at frequencies equal to the frequency offsets $\delta_1$ and $\delta_2$; and the calculation, for each point of the spatial field from the ratio of the amplitudes of the first band and of the second band, of the amplitude z of the vibration of the object.

The applicant has demonstrated that, by virtue of the method thus described, a significantly improved signal-to-noise ratio of measurements of vibration amplitudes could be obtained, notably by virtue of the simultaneous measurement of the bands of the frequency spectrum of the holograms. Very good results are obtained by working on one of the first modulation bands of the signal wave (q=±1) and with a reference wave exhibiting two components offset in frequency. It is also possible to increase the signal-to-noise ratio by increasing the number of components of the reference wave. By working on modulation bands of higher order, it is also possible to access greater vibration amplitudes.

Generally, $\gamma_1$ and $\gamma_2$ can be written respectively $p_1/N-1/2$ and $p_2/N-1/2$ where N is the number of interferograms in a set of interferograms acquired by the two-dimensional optoelectronic detector and $p_{1,2}=1, \ldots N$. According to a variant, $\gamma_1$ and $\gamma_2$ are of different norms to avoid crosstalk effects on the frequency spectrum of the optical beats between the frequency components of the reference wave and of the signal wave.

For example, the reference wave will be able to comprise at least one third component $E_{LO3}$ of frequency $\omega_3$, the frequency $\omega_3$ being offset from the frequency $\omega_L$ of the laser wave by a determined quantity $\delta_3=\gamma_3\omega_s+q\omega$, where q is a relative integer and $-0.5\leq\gamma_3\leq0.5$. In this case, the optical beats spectrum between the frequency components of the reference wave and of the signal wave comprises three bands at frequencies equal to the frequency offsets $\delta_1$, $\delta_2$ and $\delta_3$ and the calculation for each point of the spatial field of the amplitude z of the vibration of the object will be able to be performed from the ratio of the amplitudes of the first band and of the second band and from the ratio of the amplitudes of the first band and of the third band.

According to a variant, the method comprises the emission of a laser wave of frequency $\omega_1$, and the separation of the laser emission wave to form the object illumination wave and a second wave sent to an optical frequency shift optoelectronic device to form the reference wave, thus making it possible to form mutually coherent illumination and reference waves.

According to a variant, the vibration of the object can result from forced excitation of the object at said frequency $\omega$. It is then possible, by virtue of the method thus described, to determine, in addition to the vibration amplitude, the phase delay between the vibration phase of the object and the phase of the excitation signal, and do so from the ratio of the amplitudes of the first band and of the second band of the frequency spectrum of the optical beats between the frequency components of the reference wave and of the signal wave.

According to a variant, in the case of a forced excitation of the object, the excitation frequency is temporally variable in a continuous manner between a lower excitation frequency $\omega_I$ and an upper excitation frequency $\omega_F$ for a given time (T), the acquisition and the processing of the interferograms being performed during said time. The variation of the excitation frequency is for example linear between the lower and upper values. This continuous variation of the excitation frequency, simultaneously with a variation of one of the reference wave offset frequencies, allows for a locking of the phase delay of the vibration relative to the excitation, allowing for a more accurate measurement of the phase delay.

Alternatively, the method can also be applied in the case of an object exhibiting a vibration frequency spectrum. The acquisition and the processing of the interferograms are then performed to obtain the amplitude z of vibration of the object at least one vibration frequency $\omega$ contained in the spectrum. This method then makes it possible to establish, for example, mappings of vibrating objects and to determine resonant points, notably in the context of laser vibrometry for non-destructive testing.

According to a second aspect, the invention relates to a digital holography device for detecting the amplitude z of vibration of an object at a vibration frequency $\omega$, comprising:

a two-dimensional optoelectronic detector of temporal bandwidth $\omega_s$;

means for generating two mutually coherent laser waves, an object illumination laser wave of frequency $\omega_L$ and a reference wave, the field of the reference wave exhibiting at least one first and one second components of frequencies $\omega_1$, $\omega_2$ offset from the frequency $\omega_L$ of the laser wave respectively by a determined quantity $\delta_1$, $\delta_2$, with $\delta_1=\gamma_1\omega_s$ and $\delta_2=q\omega+\gamma_2\omega_s$, where q is a relative integer and $-0.5\leq\gamma_1$, $\gamma_2\leq0.5$;

means for combining the reference wave and a signal wave from the object on the two-dimensional optoelectronic detector, the reference and signal waves exhibiting an angular shift, the acquisition of the interference signal of the signal and reference waves by the two-dimensional optoelectronic detector resulting in a set of interferograms; and means for processing the interferograms comprising:

means for calculating holograms of the object obtained from each of the interferograms, a hologram being defined by the complex amplitude of the signal wave in a given spatial field of a plane of the object;

means for calculating the time-frequency Fourier transform of the complex amplitudes of said holograms, making it possible to obtain, at each point of the spatial field, a frequency spectrum of the optical beats between the frequency components of the reference wave and of the signal wave, the optical beats spectrum comprising at least two bands at frequencies equal to the frequency offsets $\delta_1$ and $\delta_2$; and means for calculating, at each point of the spatial field from the amplitudes of the first band and of the second band, the amplitude z of the vibration of the object.

According to a variant, the device comprises a laser emission source at the frequency $\omega_L$, means for splitting the laser emission wave to form the object illumination wave and a second wave and an optical frequency shift optoelectronic device, intended to receive said second wave to form the reference wave.

According to a variant, the means for splitting the laser wave are fibers.

For example, the optical frequency shift optoelectronic device comprises two acousto-optical modulators working at predetermined frequencies on opposite orders of diffraction to form said reference wave.

Alternatively, the optical frequency shift optoelectronic device comprises a Pockels cell. The Pockels cell offers the advantage of being less costly than acousto-optical modulators and of not requiring complex electronics.

According to a variant, the device further comprises a means for exciting the object at the given vibration frequency ω.

According to a variant, the two-dimensional optoelectronic detector is a camera of CCD or CMOS type.

BRIEF DESCRIPTION OF THE DRAWINGS

Other advantages and features of the invention will become apparent on reading the description, illustrated by the following figures which represent.

DETAILED DESCRIPTION

Figure 1:
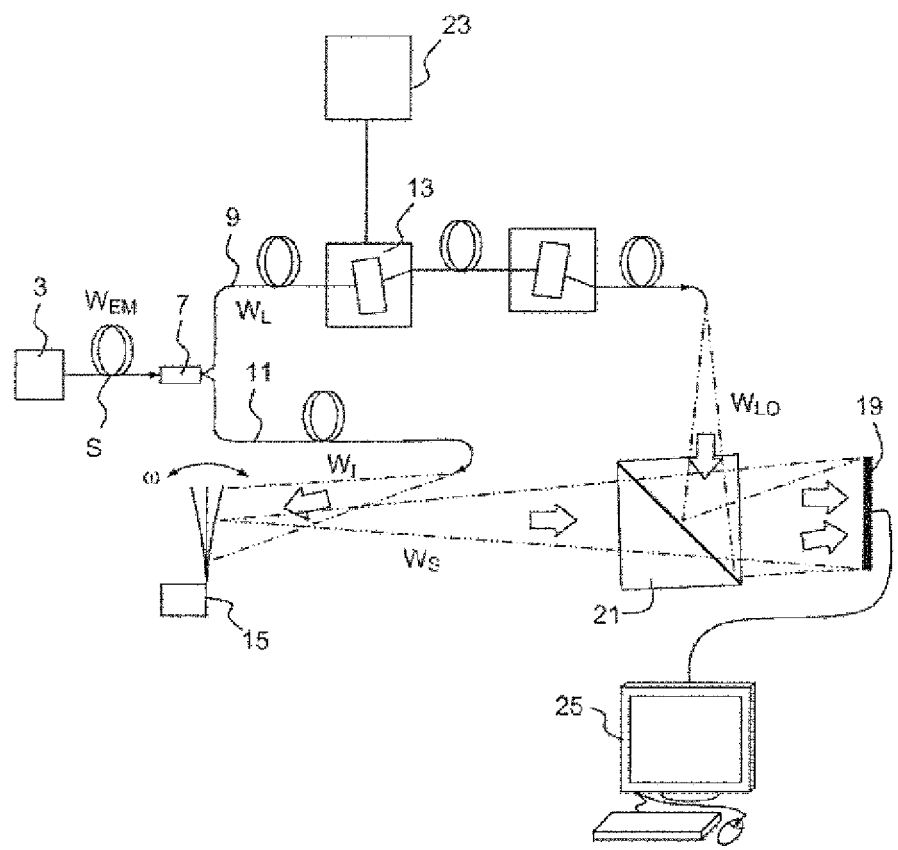
FIG. 1, a diagram of an exemplary digital holography device according to the invention.

FIG. 1 illustrates a diagram of an exemplary digital holography device according to the invention. In this example, the device is fibered. The device makes it possible to record and process interferograms of an object exhibiting at least one vibration frequency w, in order to determine the amplitude and/or the phase of vibration thereof. Hereinafter in the application, the term "vibration frequency" ω will simply be used to express the angular frequency for pulsation). The vibration phase is more specifically defined, in the case of an object subjected to a forced sinusoidal excitation, by the phase delay relative to the excitation phase. The capacity to measure vibration amplitudes of very low amplitudes of an object and the phase of the vibration of the object subjected to a forced vibration can make it possible to give very fine information on the nature of the object, such as its mechanical integrity, its quality and, if appropriate, its damage state. For this, the device according to the invention comprises means 3, 7 for generating two mutually coherent waves, an object illumination wave $W_I$ and a reference wave $W_{LO}$. In other words, the illumination wave $W_I$ and the reference wave $W_{LO}$ exhibit a phase relationship with the illumination wave that are mutually non-random. The device further comprises a two-dimensional detector 19 of temporal bandwidth $\omega_s$.

Advantageously, the generation means of the device according to the invention comprise a temporally coherent source 3, for example a laser source, emitting an emission wave $W_{EM}$ having an optical frequency $W_L$. The laser source is, for example, a laser diode emitting at an emission wavelength in the visible or near infrared spectral band, for example a fibered laser diode. The generation means of the device according to the invention further comprise a beam splitter 7, making it possible to form, from the emission wave $W_{EM}$, the object illumination wave $W_I$ and a second wave $W_L$, each having the optical frequency $\omega_L$. In the example of FIG. 1, the beam splitter 7 comprises a fiber coupler, making it possible to couple the emission wave $W_{EM}$ from an output optical fiber 5 of the emission source 3 into two optical fibers 9, 11 in order to form the illumination wave $W_I$ and the second wave $W_L$. The illumination wave $W_I$ lights the object 15 that is to be examined, either in reflection mode, or in transmission mode. The wave from the object, backscattered or transmitted, is called signal wave hereinafter in the application and denoted $W_S$ in FIG. 1.

The vibration of the object 15 resulting for example from a forced excitation of the object at the frequency ω brings about a modulation of the phase φ(t) of the temporal part of the field E of the signal wave $W_S$ due to the variation of the optical path between the vibrating object 15 and the detector 19. This leads to the appearance of optical side bands of complex amplitudes $\epsilon_n$ at the harmonics of the vibration frequency ω of the object. The modulation of the phase φ(t) as a function of time t can take the form $\phi(t)=\phi_0 \sin(\omega t+\psi)$, where $\phi_0=4\pi z/\lambda$ is the modulation amplitude, expressed as a function of the vibration amplitude z of the object and of the wavelength λ of the emission wave $W_{EM}$ and ψ is the mechanical phase delay of the vibration signal relative to the excitation signal. Thus, the optical field E of the signal wave $W_S$ can be written as $E=\Sigma_n E_n$, $E_n=\epsilon_n e^{i(\omega_L+n\Omega)t}$ and n being a relative integer, $n \in [-\infty, \infty]$. The quantities $\epsilon_n=\epsilon J_n(\phi_0)e^{in\psi}$ are the complex amplitudes of the frequency components of order n of the signal wave, with ε being the complex amplitude of the optical field of the signal wave and $J_n$ being the first species Bessel functions. There is said to be a non-offset component $E_0$ of the field E of the signal wave for n=0 and side bands for the components $E_n$ of the field E of the signal wave, where n=1, −1, 2, −2, etc. It is then possible to deduce complex amplitudes of the frequency components of order 0 and 1 of the signal wave, the vibration amplitude z of the object and the phase delay ψ by the equation:

$$\frac{\varepsilon_1}{\varepsilon_0} \approx \frac{2\pi}{\lambda} z e^{i\psi}. \tag{1}$$

The equation (1) is valid for vibration amplitudes very much lower than the wavelength λ of the emission wave.

The result thereof is notably an expression of the vibration amplitude z of the object as a function of the relative amplitude of the first band relative to the non-offset component according to the equation:

$$z \approx \frac{\lambda}{2\pi} \frac{|s_1|}{|\varepsilon_0|} \tag{2}$$

In the example illustrated in FIG. 1, the means for generating object illumination and reference waves further comprise a frequency shift optoelectronic device 13, intended to receive the second wave $W_L$ in order to offset its optical frequency $\omega_L$, to form the reference wave $W_{LO}$ and a control means 23 for the frequency shift optoelectronic device 13. The frequency-shifted reference wave $W_{LO}$ is called local oscillator hereinafter in the description. The frequency offset $\omega_L$ of the reference wave allows for a digital demodulation of the interferograms at a demodulation frequency contained in the temporal bandwidth $\omega_s$ of the optoelectronic detector, which corresponds to its acquisition rate. According to the present invention, the local oscillator, or reference wave, exhibits a first frequency $\omega_1$ and at least one second frequency $\omega_2$, the frequencies being offset from the emission frequency $\omega_L$, by a determined quantity $\delta_j$, j=1 ... m, such that, upon the demodulation of the interferograms, the non-offset component of the field of the signal wave and the side bands that are useful for the determination of the vibration amplitude z of the object are contained in the bandwidth $\omega_s$ of the camera. Thus, the field of the local oscillator can be written $E_{LO} = \Sigma_j E_{LOj}$, where $E_{LOj}$ is the component j=1 ... m taking the form $E_{LOj} = \epsilon_{LOj} e^{i\omega_L t} e^{i\delta_j t}$, with $\delta_j$ being the frequency offset. As will be explained in more detail hereinbelow, the applicant has demonstrated that a local oscillator with two frequencies (m=2), hereinafter in the description called "dual local oscillator", makes it possible to obtain a significantly better signal-to-noise ratio for the measurement of the vibration amplitude or of the phase delay than those obtained in the prior art and therefore notably achieve measurements of very low vibration amplitudes. By choosing for the local oscillator a greater number of offset frequencies (m>2), it is possible to further increase the signal-to-noise ratio. For example, in the case of a dual local oscillator, the offset frequencies of the reference wave $W_{Lo}$ will be able to be given by $\omega_1 = \omega_L + \delta_1$ and $\omega_2 = \omega_L + \delta_2$, with $\delta_1 = \gamma_1 \omega$ and $\delta_2 = q\omega_s + \gamma_2 \omega_s$, where q is a relative integer and $-0.5 \le \gamma_1, \gamma_2 \le 0.5$.

According to a variant, $\gamma_1, \gamma_2$ of different norms are chosen to avoid crosstalk effects on the frequency spectrum of the optical beats between the reference wave and the signal wave.

According to a variant, the frequency shift optoelectronic device 13 can comprise two acousto-optical modulators (AOM) operating at determined frequencies on opposite diffraction orders to obtain the offset frequencies of the reference wave. The control means 23 can comprise a digital synthesizer IC making it possible to program the synthesized frequencies of the control signals of the AOMs. The offset frequencies can thus be easily adapted to the vibration frequency e of the object.

According to a variant, the frequency shift optoelectronic device 13 can comprise a Pockels cell, making it possible to generate the local oscillator at the frequencies sought. More specifically, the Pockels cell is controlled by a signal intended to create at least two offset frequencies of the reference wave $W_{LO}$. This signal can, for example, be a linear sweep of control voltage with time, the slope of which switches sequentially between two values at least once during the acquisition time of an image, the two slopes being the two frequency offsets $\delta_1$ and $\delta_2$ of the dual local oscillator.

The interference between the reference wave or local oscillator $W_{LO}$ and the signal wave $W_S$, recombined using a combination means 21, for example a splitter cube, leads to interference figures which are acquired by the two-dimensional detector 19. The combination means 21 is arranged in such a way that the two waves interfere with an angle θ of the order of a degree. This off-axis setup makes it possible, when processing the recorded interferograms, to perform a spatial filtering in the range of spatial frequencies k in order to eliminate the conjugated parasitic image and the order 0 which appear when reconstructing the holograms. By virtue of the choice of the frequencies of the local oscillator, the interference between the signal wave and the reference wave give rise to optical beats at frequencies lying in the temporal bandwidth $\omega_s$ of the detector 19.

Figures 2A, 2B, 2C:
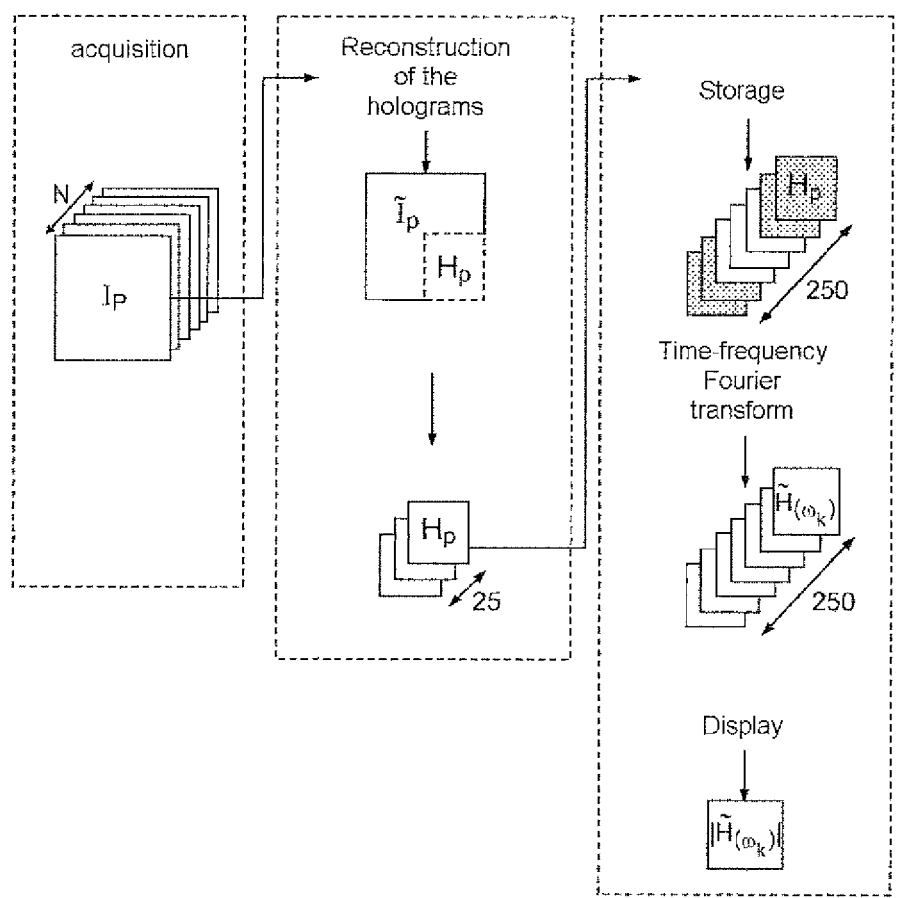
FIGS. 2A to 2C, diagrams illustrating interferogram processing steps in an exemplary digital holography method according to the invention.

The digital holography device according to the invention also comprises means 25 for processing the interferograms recorded by the two-dimensional detector 19. FIGS. 2A to 2C schematically illustrate the steps implemented to calculate the holograms of the object, then making it possible to access the amplitude z and/or the phase ψ of vibration of the object. A number N of interferograms $I_p$ is recorded per time interval by the two-dimensional detector, as illustrated by FIG. 2A. For example, 256 images are acquired at a frequency $\omega_s/(2\pi) = 20$ Hz. The offset frequencies of the reference wave are chosen such that $\gamma_1$ and $\gamma_2$ are respectively equal to $p_1/N - 1/2$ and $p_2/N - 1/2$ where $p_{1,2} = 1, \ldots N$. The processing means then makes it possible to calculate, in a reconstruction step, a hologram of the object from each recorded interferogram. An interferogram recorded by the detector has the form $$I_p = \left| \sum_n E_n + \sum_j E_\omega \right|^2. \tag{3}$$

The reconstruction of the hologram is done for example, in a known manner, by Fresnel transform of the interferogram $I_p$ making it possible to obtain, for each interferogram, a hologram with complex values $\tilde{I}_p = \text{Fresnel}\{I_p\}$ in a given spatial field of a plane of the object. Each hologram is thus defined by the complex amplitude of the signal wave in the given spatial field of the object. Advantageously, only an off-center part $H_p$ (called off-axis) of the images $\tilde{I}_p$ is retained subsequently, as illustrated in FIG. 2B, the off-axis holograms $H_p$ being obtained by digital filtering in the space of the spatial frequencies, to keep only the useful diffraction order in the reconstruction.

The holograms $H_p$ are stored (FIG. 2C) then a time-frequency Fourier transform of the complex amplitudes of the holograms $H_p$ is calculated, for each point of the field, in order to obtain the frequency spectrum $\tilde{H} = FT\{H\}$, shown schematically in FIG. 2C. The component k of the Fourier transform can be written as follows:

$$\tilde{H}(\omega_k) = \Sigma_{p=1}^N H_p \exp(-2ipk\pi/N) \tag{4}$$

There is thus obtained a frequency spectrum $|\tilde{H}(\omega_k)|$ of the optical beats between the frequency components of the reference wave $W_{LO}$ and of the signal wave $W_S$ for each point of the field. It is shown that each component $\tilde{H}(\omega_k = \gamma_k \omega_s)$ can be written:

$$\tilde{H}(\omega_k = \gamma_k \omega_s) = K\epsilon_{k-1} \epsilon^*_{LOk}, \tag{5}$$

where K is a constant. For example, in the case of the dual local oscillator, $\tilde{H}(\gamma_1 \omega_s) = K\epsilon_0 \epsilon^*_{LO1}$ and $\tilde{H}(\gamma_2 \omega_s) = K\epsilon_1 \epsilon^*_{LO2}$.

Figure 3A:
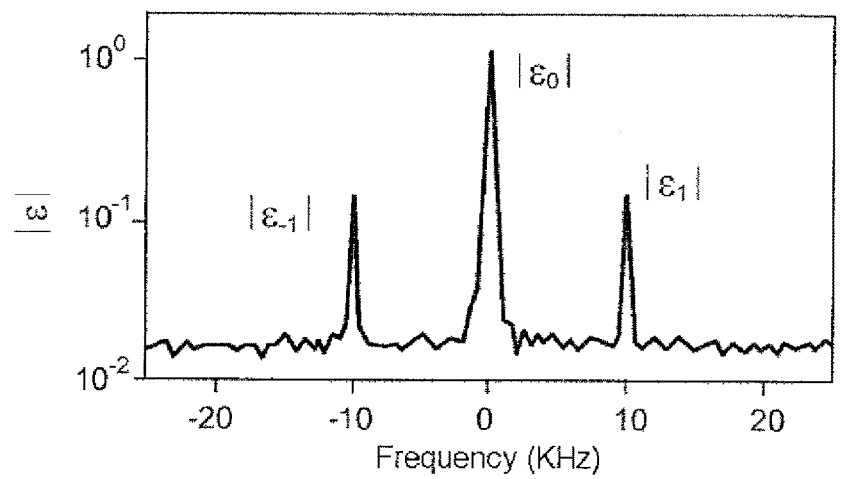
FIGS. 3A to 3C, diagrams showing, in an exemplary embodiment, frequency spectrum measurements of the field of the signal wave (FIG. 3A), of the field of the reference wave (FIG. 3B) and of the optical beats between the frequency spectra of the fields of the signal and reference waves (FIG. 3C), obtained by the digital holography method according to the invention.
Figure 3B:
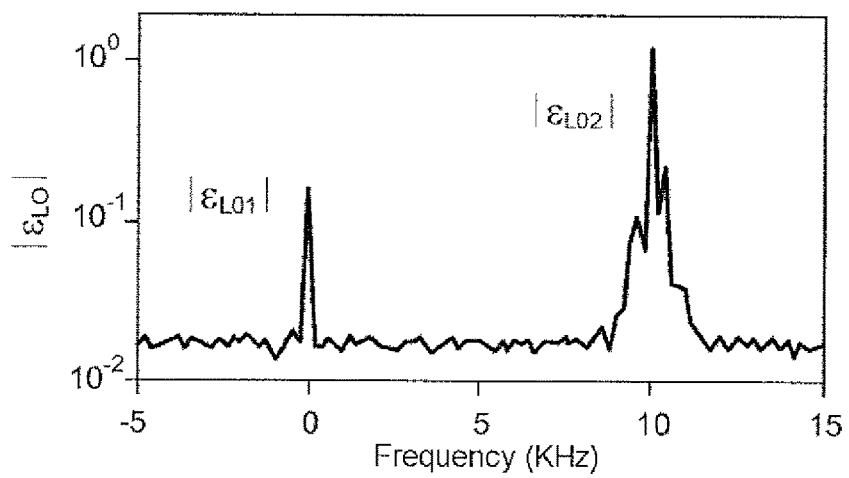
Figure 3C:
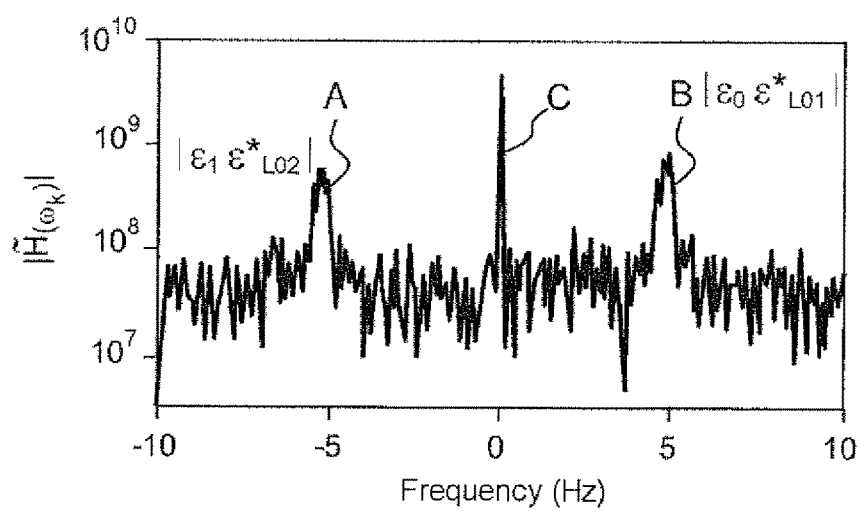

FIGS. 3A to 3C show diagrams representing measured frequency spectra of the amplitude E of the field of the signal wave $W_S$ (FIG. 3A), of the amplitude $E_{LO}$ of the field of the reference wave $W_{LO}$ (FIG. 3B) and of the optical beats between the frequency components of the reference wave $W_{LO}$ and of the signal wave $W_S$ for a given point of the field (FIG. 3C) in an exemplary implementation.

In this example, the local oscillator is dual and comprises two offset frequencies $\omega_1 = \omega_L + \omega_s/4$ and $\omega_2 = \omega_L + \omega - \omega_s/4$ obtained for example by means of two acousto-optical modulators, of which one operates at the carrier frequency $\omega_c$, and the second operates at the frequencies $\omega_c-\omega_s/4$ and $\omega_c+\omega_c+\omega+\omega_s/4$. The acousto-optical modulators are, for example, Bragg cells operating at the carrier frequency $\omega_c/(2\pi)$=80 MHz. The emission source is a laser diode operating at 532 nm. The signal and reference waves are combined on the detector with an angle of a few degrees. The detector is a CCD camera of acquisition frequency $\omega_s/(2\pi)$=20 Hz. The object is a piezoelectric actuator exhibiting an off-plane oscillation of frequency $\omega/(2\pi)$=10 kHz. A variable voltage of between $10^{-2}$ V and 10 V is applied to the piezoelectric actuator to vary the vibration amplitude. For each voltage, a set of 256 interferograms $I_p$ is acquired by the CCD camera and then processed according to the method described above.

FIGS. 3A and 3B illustrate the frequency spectra of the signal wave and of the reference wave (local oscillator). In FIG. 3A, the non-offset component $|\epsilon_0|$ of the signal wave (brought to the frequency 0) and the side bands $|\epsilon_1|$ and $|\epsilon_{-1}|$ are observed at the frequencies $+\omega$ and $-\omega$ respectively. In FIG. 3E, the side bands of the local oscillator, respectively $|\epsilon_{LO1}|$ and $|\epsilon_{LO2}|$ can be seen, corresponding respectively to offsets relative to the frequency $\omega_1$, of the laser emission wave of $\delta_1=\omega_s/4$ and $\delta_2=\omega-\omega_s/4$.

Each interferogram $I_p$ formed in the plane of the detector has an expression given by the equation (3) above. Upon the detection, only the frequency components lying between $\pm\omega_s/2$ are visible to the detector. In the above example, the detector records the non-offset component $|\epsilon_0|$ and the first offset component $|\epsilon_1|$ of the signal wave modulated by the vibration of the object simultaneously, by virtue of the transposition of the frequencies of the signal wave $W_S$ in the temporal bandwidth of the detector by means of the reference wave $W_{LO}$. Thus, in FIG. 3C, the amplitude of the band A is proportional to $|\epsilon_{LO2}\epsilon_1|$ and the amplitude of the band B is proportional to $à|\epsilon_{LO2}*\epsilon_0|$, the band C corresponding to the static contribution to the spectrum of the beats. The three contributions A, B and C lie within the temporal bandwidth $\omega_s$ of the detector, the other contributions of the equation (3) are not detected.

For $z<\lambda$, and by using the equations (2) and (5), it is possible to calculate the vibration amplitude z of the object from the relationship $$z \approx \frac{\lambda}{2\pi} \frac{\alpha}{\beta} \frac{|\tilde{H}(\omega s/4)|}{|\tilde{H}(-\omega s/4)|}, \quad (6)$$

where $\alpha$ and $\beta$ are the respective contributions of the components at $\omega_s/4$ and $-\omega_s/4$ of the local oscillator and $\tilde{H}(\omega s/4)$ and $\tilde{H}(-\omega s/4)$ are given respectively, according to the equation (5), by the amplitude of the bands A and B in FIG. 3C. Thus, according to the equation (6), it is possible to access the vibration amplitude z of the object by calculating the ratio between the amplitude of the bands A and B. Advantageously, the ratio of the complex amplitudes $\epsilon_0$ and $\epsilon_1$ is averaged spatially over all of the image of the object.

For an object subjected to a forced sinusoidal excitation of given frequency $\omega$, the ratio between the amplitude of the bands A and B also gives access to the mechanical phase delay $\psi$ of the vibration relative to the excitation signal, by taking into account the equations (1) and (5), $$\psi - \psi_0 = \arg\left(\frac{\tilde{H}(\omega s/4)}{\tilde{H}(-\omega s/4)}\right), \quad (7)$$

where $\psi_0$ is a reference constant phase.

The applicant has demonstrated that the simultaneous acquisition of the amplitudes of the side bands represented by the bands A and B in FIG. 3C allowed for an excellent signal-to-noise ratio in the measurement of the amplitude and of the phase of the vibration. The signal-to-noise ratio can be further improved by proceeding with a spatial average, over the spatial measurement field or a part of the spatial measurement field, of the ratio of the measured band amplitudes.

Figure 4:
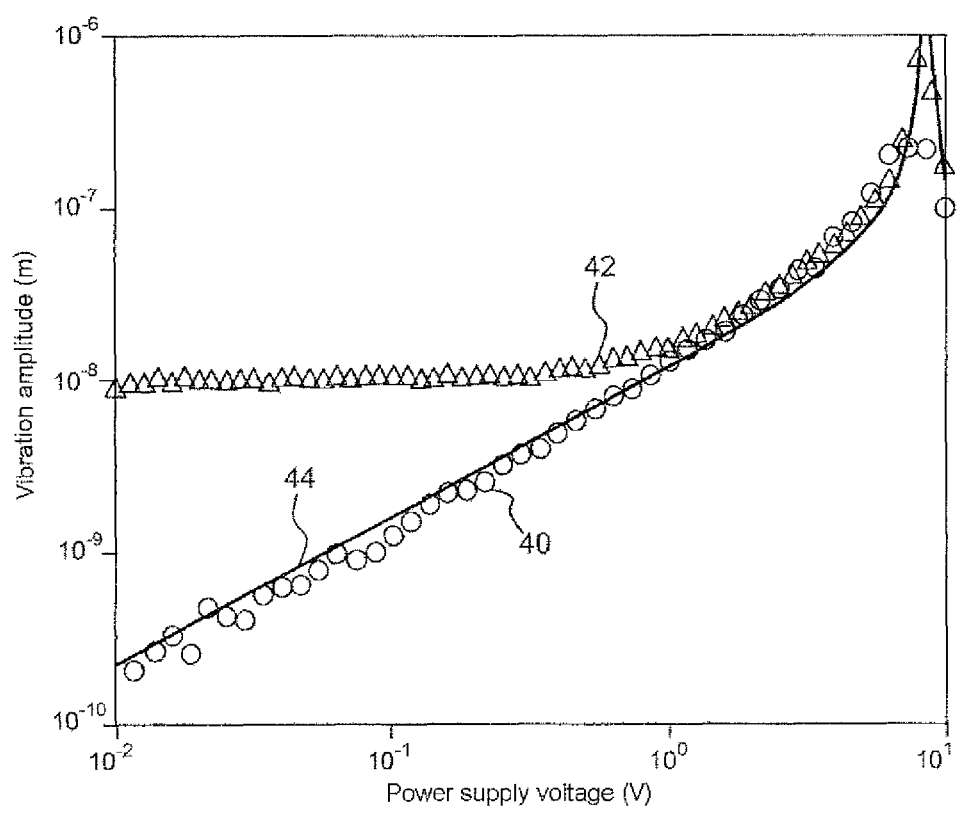
FIG. 4, a diagram showing comparative curves of measurements of amplitude z of vibration of an object, performed respectively using the method according to the invention and according to a method of the prior art.

FIG. 4 shows, according to the exemplary embodiment above, results of measurement of the vibration amplitude z of the piezoelectric actuator when the power supply voltage of the actuator varies. More specifically, the points 40 represent the vibration amplitude values in meters (m) measured with the method using the dual local oscillator as described above, as a function of the power supply voltage in volts (V) of the piezoelectric actuator. By way of comparison, the diagram also shows the result of measurements of the vibration amplitude 42 performed according to a prior art method, in which the non-offset component and the first offset component of the signal wave have been recorded sequentially, with other measurement conditions equal to those of the method according to the invention (same object, frequency offsets $\delta_1$ and $\delta_2$, power supply voltages). The method according to the present invention makes it possible to access vibration amplitudes of the object of the order of an Angstrom ($10^{-10}$ m), whereas the minimum amplitude that can be accessed by the prior art method is of the order of 10 nm ($10^{-8}$ m). For the method according to the invention, experimental measurement points 40 and the result of the theoretical calculation (continuous line 44) using the equation (6) are represented.

The use of at least two offset frequencies for the reference wave $W_{LO}$ makes it possible to obtain a perfect phase agreement, at each point, between the hologram corresponding to the non-frequency offset component $\epsilon_0$ and the hologram corresponding to the frequency offset component $\epsilon_{\pm1}$. By virtue of this phase agreement, the signal-to-noise ratio can be increased relative to a measurement of z using two sequential frequency offsets, and vibrations of the object of very low amplitude are accessible to the measurement.

Figure 5:
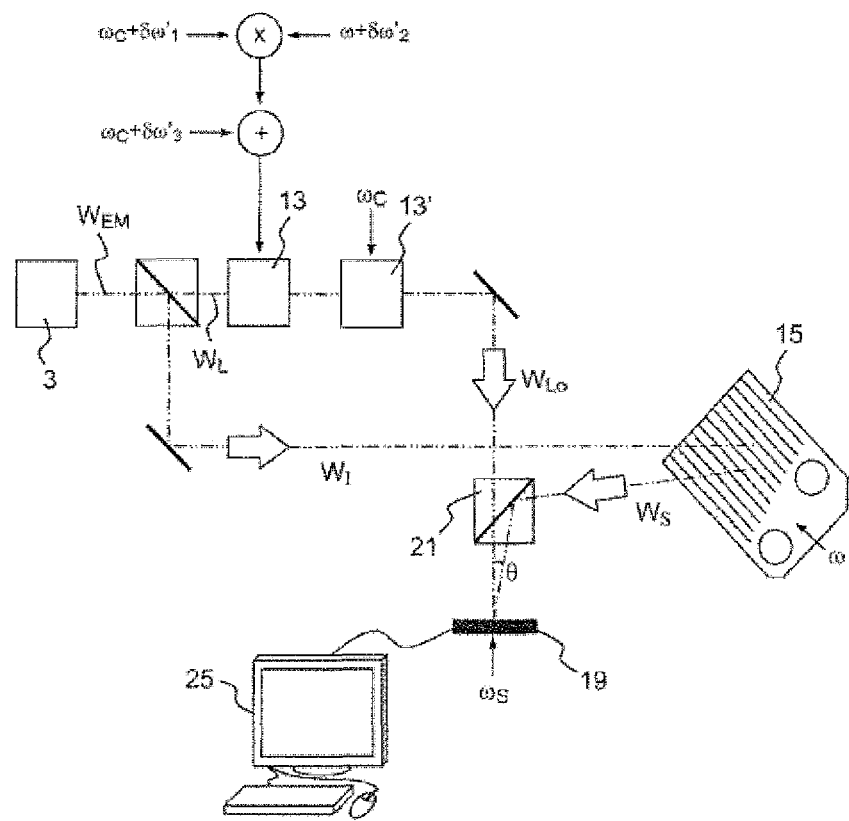
FIG. 5, a diagram illustrating a particular exemplary embodiment of a device according to the invention.

The applicant has demonstrated, experimentally, the feasibility of a spatial mapping of the vibration amplitude and the vibration phase, with an excellent accuracy. The experimental setup is represented in FIG. 5. For this experiment, the object used is a lamellophone with metal plates, the plates of which exhibit mutually different resonance frequencies, a function notably of the weight and of the length of each plate. A piezoelectric actuator makes it possible to excite the plates of the lamellophone at a variable vibration frequency $\omega$. The elements used for the experimental setup of FIG. 5 can be substantially identical to those described with reference to FIG. 1. In this example however, to gain in terms of signal-to-noise ratio, the reference wave $W_{LO}$ (local oscillator) exhibits three offset frequencies $\omega_1$, $\omega_2$ and $\omega_3$ offset from the emission frequency $\omega_L$ respectively by a quantity $\delta_1$, $\delta_2$ and $\delta_3$, the frequency offsets being chosen to allow for a demodulation of the interferograms in the temporal bandwidth $\omega_s$ of the detector, for example a CCD camera. For example, $\delta_n=(n-2)\omega-\omega_s\gamma_n$, with $\omega_s$ being the acquisition frequency of the detector, n=1, 2, 3 and $-0.5\leq\gamma_n\leq0.5$. The offset frequencies are obtained for example by means of two acousto-optical modulators (13, 13') arranged to operate around $\omega_c(2\pi)$=80 MHz and controlled by a radio frequency digital synthesizer making it possible to generate a carrier frequency $\omega_c$ and three offset frequencies $\Omega_c+\delta\Omega'_1$, $\Omega_c+\delta\Omega'_2$, and $\Omega_c+\delta\Omega'_3$ and making it possible to obtain the frequencies $\omega_1$, $\omega_2$ and $\omega_3$ of the local oscillator. In the same way as previously, the camera makes it possible to acquire, at its acquisition frequency $\omega_s$, a set of N interferograms which are processed in such a way as to obtain a frequency spectrum of the optical beats between the local oscillator and the signal wave.

Figure 6A:
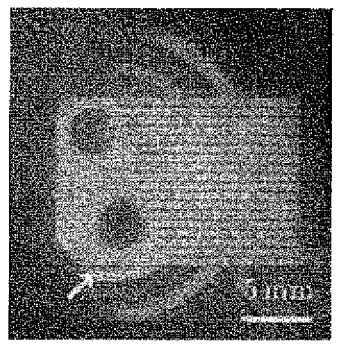
FIGS. 6A to 6D, holograms of an object obtained with the device of the example of FIG. 5.
Figure 6B:
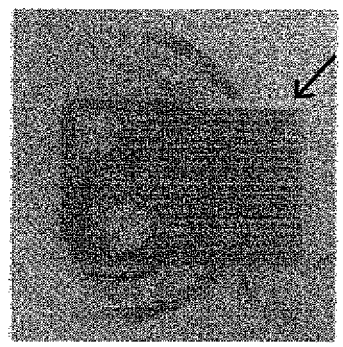
Figure 6C:
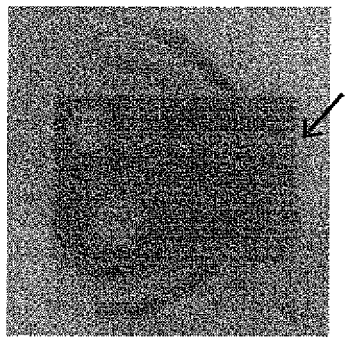
Figure 6D:
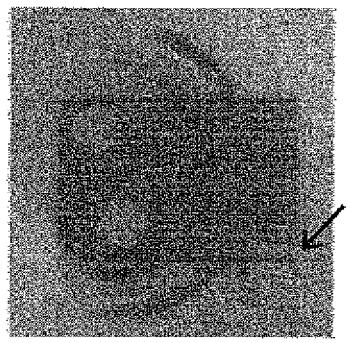

By varying the excitation frequency $\omega$, each blade of the lamellophone is made to vibrate in succession at its resonance frequency. In this experiment, the excitation frequency $v=\omega/(2\pi)$ of the piezoelectric actuator varies from 0 to 3 kHz, in steps of 1 Hz. 3000 sequences of N=8 interferograms are acquired at a frequency $\omega_s/(2\pi)=20$ Hz, and processed according to the method described above. The frequency offsets $\gamma_1\omega_s$, $\gamma_2\omega_s$ and $\gamma_3\omega_s$ are respectively −5 Hz, −2.5 Hz and −7.5 Hz. FIGS. 6A to 6D show the frequency components of the holograms $\tilde{H}(\omega_k)$ as defined by the equation (4) above and computed over all of the points of the object. More specifically, FIG. 6A shows the non-offset component $|\tilde{H}(\gamma_1\omega_s)|$ of the hologram of the lamellophone, proportional to the amplitude of the non-offset component $|\epsilon_0|$ of the signal wave. FIGS. 6B to 6D represent the frequency component $|\tilde{H}(\gamma_1\omega_s)|$ of the hologram of the lamellophone proportional to the amplitude of the side band $|\epsilon_1|$ of the signal wave, obtained respectively at three different excitation frequencies $\omega$, corresponding respectively to the resonance frequencies of the blades indicated by an arrow in each of the figures. The excitation frequencies $v=\omega/(2\pi)$ are respectively 541 Hz, 1006 Hz and 2211 Hz for FIGS. 6B, 6C and 6D. A qualitative observation of the resonance frequencies of the different blades is thus revealed, by varying the excitation frequency of the lamellophone and by adapting an offset frequency of the local oscillator to the excitation frequency.

As explained previously in the case of the dual local oscillator, a quantitative measurement of the vibration amplitude z and of the phase delay $\psi$ at a point of the object can then be made from the complex amplitudes of the different bands of the frequency spectrum of the holograms measured simultaneously by virtue of the multiple offset frequencies of the local oscillator. In the example of FIG. 5, the local oscillator exhibits three offset frequencies and the vibration amplitude z as well as the phase delay $\psi$ can be deduced from two of the three bands $|\tilde{H}(\gamma_1\omega_s)|$, $|\tilde{H}(\gamma_2\omega_s)|$ and $|\tilde{H}(\gamma_3\omega_s)|$ of the frequency spectrum of the holograms or from the three bands of the frequency spectrum of the holograms, for example by the equations:

$$z \approx \frac{\lambda}{4\pi}\left(\left|\frac{\tilde{H}(\gamma_2\omega_s)}{\tilde{H}(\gamma_1\omega_s)}\right| + \left|\frac{\tilde{H}(\gamma_3\omega_s)}{\tilde{H}(\gamma_1\omega_s)}\right|\right), \quad (8)$$

$$\psi - \psi_0 = \frac{1}{2}\left[\arg\left(\frac{\tilde{H}(\gamma_2\omega_s)}{\tilde{H}(\gamma_1\omega_s)}\right) + \arg\left(\frac{\tilde{H}(\gamma_1\omega_s)}{\tilde{H}(\gamma_3\omega_s)}\right)\right], \quad (9)$$

by taking into account the equations (1), (2) and (5).

Figure 7:
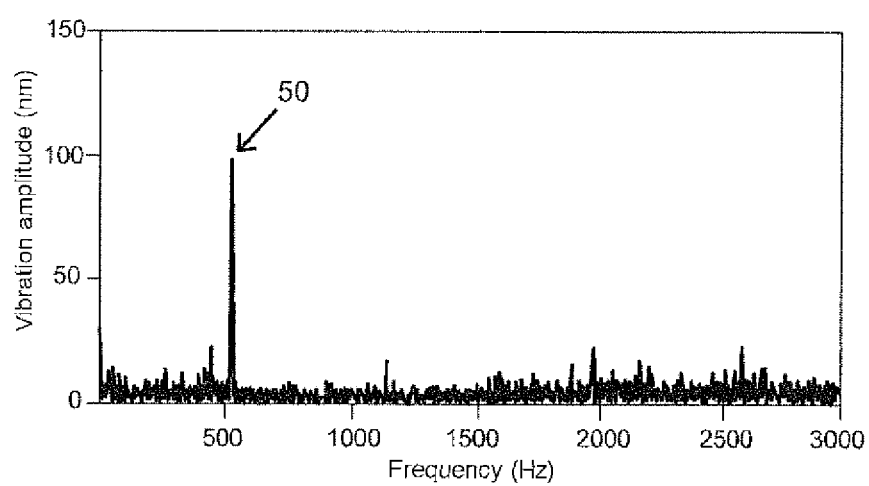
FIG. 7, a diagram representing, as a function of the excitation frequency of the object, the measured amplitude of vibration at a given point of the object.

FIG. 7 shows the vibration amplitude of the longer blade of the lamellophone (indicated by the arrow in FIG. 6B) as a function of the excitation frequency v. At the resonance frequency of 541 Hz of this blade, the vibration amplitude 50 is maximum.

By increasing the number of components of the reference wave and working on the higher order modulation bands, it is possible to access greater vibration amplitudes, typically up to 1 millimeter.

According to a variant, in order to lock the constant phase $\psi_0$ of one measurement to the other and accurately determine the mechanical phase delay $\psi$, a continuous temporal variation of the excitation frequency ("chirp") is applied simultaneously to the object excitation signal and to one of the frequency offsets $\delta_n$ of the reference wave. The temporal variation of excitation is, for example, linear and is written:

$$\omega(t)=\omega_I+(\omega_F-\omega_I)t/T, \quad (10)$$

where $\omega_I$ is the lower excitation frequency, $\omega_F$ is the upper excitation frequency, and T is the time of the variation.

Figure 8A:
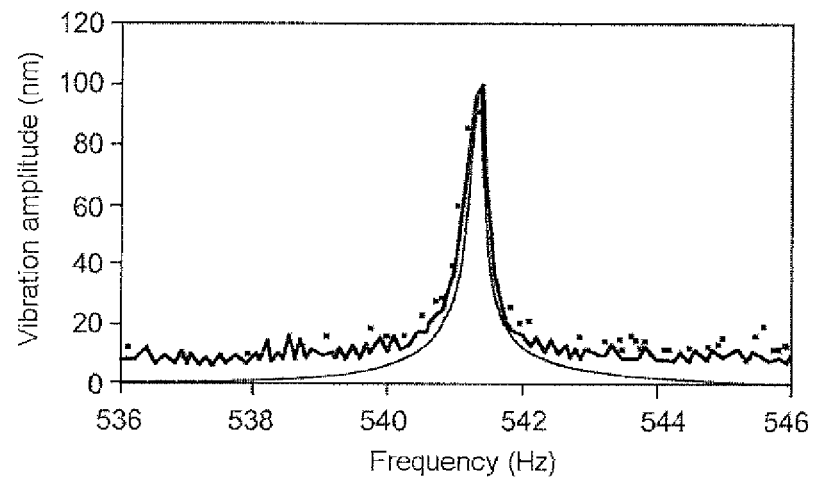
FIGS. 8A and 8B, diagrams representing, as a function of the excitation frequency of the object, respectively the vibration amplitude and the phase, the measured curves being compared to the theoretical curves.
Figure 8B:
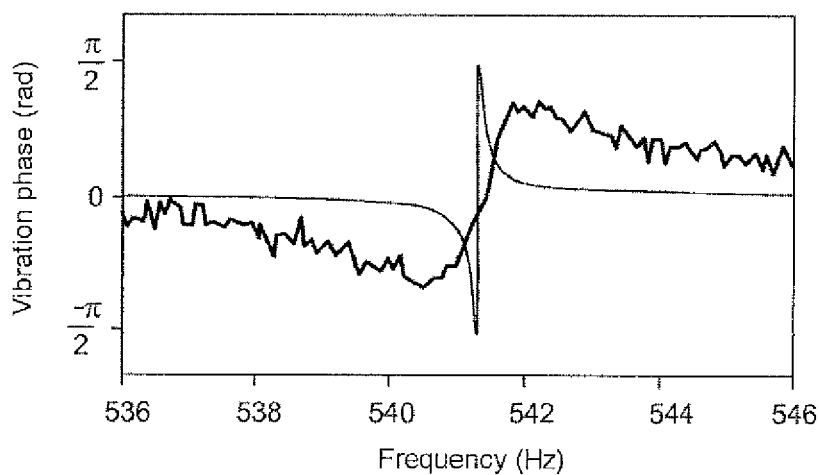

FIGS. 8A and 8B show experimental results obtained with an experimental setup according to the example of FIG. 5, as described above. The excitation frequency v varies continuously between 536 Hz and 546 Hz during a variation time T=99.2 s. This same frequency variation is applied to one of the components of the local oscillator. At each frequency $\omega(t)$, N=8 interferograms have been acquired at a rate of 20 Hz via the CCD camera, and processed according to the method of the present invention. The vibration amplitude of the longest blade of the lamellophone as a function of the excitation frequency v is shown in FIG. 8A, where the vibration amplitude is maximum at the resonance frequency of the blade concerned. FIG. 8B represents the phase shift $\psi-\psi_0$ as a function of the excitation frequency. The curve reveals a phase jump of $\pi$ at the resonance frequency.

Although described essentially through examples implementing a forced excitation of the object, the present invention applies equally to the study of vibration and more particularly of the resonance frequencies of objects exhibiting vibration spectra, for example in the context of non-destructive testing. The accurate measurements of the vibration amplitude and of the phase delay as described previously will be able to make it possible to accurately analyze in particular the resonances of the object.

Although described through a certain number of detailed exemplary embodiments, the off-axis heterodyne holography method and device according to the invention comprise different variants, modifications and refinements will become obviously apparent to those skilled in the art, given that these different variants, modifications and refinements form part of the scope of the invention, as defined by the ensuing claims.

The invention claimed is:

1. A digital holography method for detecting an amplitude of vibration of an object at, at least, one vibration frequency $\omega$, comprising:
generating an object illumination laser wave at a laser wave frequency and generating a reference wave that is coherent with the object illumination laser wave;
acquiring, by a two-dimensional optoelectronic detector having a temporal bandwidth $\omega_s$, a set of interferograms that is produced from interference of the reference wave and a signal wave from the object, wherein the signal wave and the reference wave have an angular shift, a field of the reference wave comprises a first field component at a first field component frequency and at least a second field component at a second field component frequency, the first field component frequency and the second field component frequency being offset from the laser wave frequency respectively by determined first and second frequency offset quantities $\delta_1$, $\delta_2$, with $\delta_1=\gamma_1\omega_s$ and $\delta_2=q\omega+\gamma_2\omega_s$, and q being a relative integer and $-0.5\le\delta_1$, $\delta_2\le0.5$; and processing the set of interferograms, comprising:
calculating a hologram of the object from each of the interferograms, the hologram being defined by a complex amplitude of the signal wave in a spatial field of a plane of the object;
calculating a time-frequency Fourier transform of the complex amplitude of said hologram, obtaining, at each point of the spatial field, a frequency spectrum of optical beats between frequency components of the reference wave and frequency components of the signal wave, the frequency spectrum of the optical beats comprising at least a first band and a second band for frequencies equal to the first and second frequency offset quantities $\delta_1$ and $\delta_2$; and
calculating, for the each point of the spatial field, from a ratio of amplitudes of the first band and of the second band, the amplitude of the vibration of the object.

2. The method as claimed in claim 1, wherein norms of Ti and 72 are different.

3. The method as claimed in claim 1, wherein the generating the object illumination laser wave and the generating the reference wave comprises:
emitting a laser emission wave having a laser emission wave frequency; and
separating the laser emission wave to form the object illumination laser wave and a second laser wave sent to an optical frequency shift optoelectronic device to form the reference wave.

4. The method as claimed in claim 1, further comprising exciting the object at said vibration frequency.

5. The method as claimed in claim 4, wherein the vibration frequency of the object is continuously and temporally variable between a lower vibration frequency and an upper excitation vibration frequency for a predetermined period of time, and wherein the acquiring and the processing of the interferograms are performed during said redetermined period of time.

6. The method as claimed in claim 4, further comprising calculating a phase delay between a vibration phase of the object and a phase of the excitation signal from the ratio of the amplitudes of the first band and of the second band.

7. The method as claimed in claim 1, wherein:
the vibration of the object has a frequency spectrum; and
the acquiring and the processing of the interferograms are performed to obtain the amplitude of vibration of the object at a at least, one vibration frequency of the frequency spectrum.

8. The method as claimed in claim 1, wherein the field of the reference wave comprises at least one third component of a third frequency, the third frequency being offset from the object illumination laser wave frequency by a determined third frequency offset quantity $\delta_3 = \gamma_3 \omega_s + p\omega$, and p being a relative integer and $-0.5 \leq \delta_3 \leq 0.5$.

9. The method as claimed in claim 1, wherein q=1.

10. A digital holography device for detecting an amplitude of vibration of an object at a vibration frequency $\omega$, comprising:
a two-dimensional optoelectronic detector having a temporal bandwidth $\omega_s$;
an emission source that generates an object illumination laser wave at a laser wave frequency and a reference wave that is coherent with the object illumination laser wave, a field of the reference wave having at least a first field component at a first field component frequency and one a second field component at a second field component frequency, the first and second field components frequencies being offset from the laser wave frequency respectively by determined first and second frequency offset quantities $\delta_1$, $\delta_2$, with $\delta_1 = \gamma_1 \omega_s$ and $\delta_2 = q\omega + \gamma_2 \omega_s$, and q being a relative integer and $-0.5 \leq \delta_1, \delta_2 \leq 0.5$;
a slitter that combines the reference wave and a signal wave from the object on the two dimensional optoelectronic detector, the reference wave and the signal wave having an angular shift, and thus producing an interference signal of the signal wave and the reference wave acquired by the two dimensional optoelectronic detector to rod a set of interferograms; and
a processor that processes the interferograms comprising:
a first calculating unit that calculates holograms of the object obtained from each of the interferograms, the hologram being defined by a complex amplitude of the signal wave in a give spatial field of a plane of the object;
a second calculating unit that calculates a time-frequency Fourier transform of the complex amplitude of said hologram, obtaining, at each point of the spatial field, a frequency spectrum of optical beats between frequency components of the reference wave and frequency components of the signal wave, the frequency spectrum of the optical beats comprising at least a first band and a second band for frequencies equal to the first and second frequency offset quantities $\delta_1$ and $\delta_2$; and
a third calculating unit that calculates, at the each point of the spatial field from amplitudes of the first band and of the second band, the amplitude of the vibration of the object.

11. The digital holography device as claimed in claim 10, wherein the emission source comprises:
a laser emission source that emits a laser emission wave at the laser emission wave frequency;
a beam splitter that split the laser emission wave to form the object illumination laser wave and a second wave;
an optical frequency shift optoelectronic device that receives said second wave and forms the reference wave.

12. The digital holography device as claimed in claim 11, wherein the optical frequency shift optoelectronic device comprises two acousto-optical modulators working at predetermined frequencies on opposite orders of diffraction and forms said reference wave.

13. The holographic device as claimed in claim 11, wherein the optical frequency shift optoelectronic device comprises a Pockels cell.

14. The holographic device as claimed in claim 11, wherein the beam splitter is fibered.

15. The holographic device as claimed in claim 10, further comprising a vibrator that vibrates the object at the given vibration frequency.

16. The holographic device as claimed in claim 10, wherein the two-dimensional optoelectronic detector is charge coupled device (CCD) or a complementary metal-oxide semiconductor (CMOS) came.

* * * * *